US00PP34592P2

(12) United States Plant Patent
von Tubeuf

(10) Patent No.: US PP34,592 P2
(45) Date of Patent: Sep. 13, 2022

(54) ***LOBELIA* PLANT NAMED 'KLELE20103'**

(50) Latin Name: *Lobelia erinus*
Varietal Denomination: KLELE20103

(71) Applicant: Klemm+Sohn GmbH & Co. KG, Stuttgart (DE)

(72) Inventor: Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/373,333

(22) Filed: Jul. 12, 2021

(51) Int. Cl.
*A01H 5/02* (2018.01)
*A01H 6/26* (2018.01)

(52) U.S. Cl.
USPC ..... Plt./451
CPC ..... *A01H 6/268* (2018.05)

(58) Field of Classification Search
USPC ..... Plt./451
CPC ..... A01H 6/268
See application file for complete search history.

(56) References Cited

PUBLICATIONS

UPOV hit on *Lobelia* plant named, 'KLELE20103', QZ PBR 20211319, filed Jun. 10, 2021.*
CPVO application document for QZ PBR 20211319, filed Jun. 10, 2021.*

* cited by examiner

*Primary Examiner* — Anne Marie Grunberg
(74) *Attorney, Agent, or Firm* — Weatherly IP Solutions, LLC; Barbara Campbell

(57) ABSTRACT

A new *Lobelia* plant particularly distinguished by an upright and freely branching growth habit, and blue and white bicolored flowers, is disclosed.

1 Drawing Sheet

Genus and species: *Lobelia erinus.*
Variety denomination:
'KLELE20103'.

BACKGROUND OF THE NEW PLANT

The present invention comprises a new and distinct variety of *Lobelia*, botanically known as *Lobelia erinus*, and hereinafter referred to by the variety name 'KLELE20103'. 'KLELE20103' originated from a controlled cross-pollination in July 2015 in Stuttgart, Germany between the proprietary female *Lobelia* variety 'LE-2015-5129' (unpatented) and the proprietary male *Lobelia* variety 'LE-2015-5135' (unpatented).

The seeds from the cross were sown and plants were grown in a greenhouse for evaluation, where an individual plant designated 'KLELE20103' was selected from the group. 'KLELE20103' was first vegetatively propagated via apical vegetative cuttings. 'KLELE20103' was found to reproduce true to type in successive generations of asexual propagation via apical vegetative cuttings.

SUMMARY

The following are the most outstanding and distinguishing characteristics of this new variety when grown under normal horticultural practices in Stuttgart, Germany.

1. An upright and freely branching growth habit; and
2. Blue and white bicolored flowers.

DESCRIPTION OF THE PHOTOGRAPH

This new *Lobelia* plant is illustrated by the accompanying photograph which shows the plant's overall plant habit including form, foliage, and flowers. The photograph is of a 4-month-old plant grown in a glass greenhouse in Stuttgart, Germany in March 2021. The colors shown are as true as can be reasonably obtained by conventional photographic procedures.

DESCRIPTION OF THE NEW VARIETY

The following detailed descriptions set forth the distinctive characteristics of 'KLELE20103'. The data which define these characteristics were collected from asexual reproductions carried out in Stuttgart, Germany. Data was collected on 8-week-old plants grown in a greenhouse in Stuttgart, Germany in May 2021. Color references are to The R.H.S. Colour Chart of The Royal Horticultural Society of London (R.H.S.), 5$^{th}$ edition (2007), unless otherwise noted.

Classification:

*Family.*—Campanulaceae.
*Botanical.*—*Lobelia erinus.*
*Common.*—*Lobelia.*
*Designation.*—'KLELE20103'.

Parentage:

*Female parent.*—The proprietary female *Lobelia* variety 'LE-2015-5129 (unpatented).
*Male parent.*—The proprietary male *Lobelia* variety 'LE-2015-5135' (unpatented).

Growth:

*Growth and branching habit.*—Upright, freely branching.
*Form.*—Triangular.
*Height* (*measured from the top of the soil including any flowers*).—20.0 cm.

*Width* (*horizontal plant diameter, including any flowers*).—29.0 cm.
*Time to produce a finished flowering plant.*—8 weeks.
*Outdoor plant performance.*—Very good.
*Time to initiate roots.*—2 to 3 weeks.
*Root description.*—Fine, white roots, freely branching, and dense.

Leaves:
*Arrangement.*—Alternate.
*Color.*—Immature Leaf: Upper surface: RHS 141B (Green). Lower surface: RHS 138B (Green). Mature Leaf: Upper surface: RHS 141 (Green). Lower surface: RHS 138B (Green).
*Length.*—5.0 cm to 6.0 cm.
*Width.*—2.0 cm to 2.5 cm.
*Shape.*—Elliptical.
*Margin.*—Sinuate.
*Apex.*—Obtuse.
*Base.*—Attenuate.
*Texture.*—Upper surface is slightly haired, while the lower surface is smooth.
*Venation.*—Pinnate.
*Venation color.*—Upper surface: Transparent, RHS color not available. Lower surface: RHS 143D (Green).

Stems:
*Length.*—17.0 cm.
*Diameter.*—0.2 cm.
*Internode length.*—1.0 cm to 2.0 cm.
*Texture.*—Slightly haired.
*Stem anthocyanin.*—Absent.
*Stem color.*—RHS 143A (Green).
*Peduncle.*—Length: 1.0 cm to 3.0 cm. Diameter: 0.05 cm. Texture: Smooth. Color: RHS 143A (Green).

Flower buds:
*Shape.*—Inverse drop-shaped.
*Diameter.*—0.25 cm to 0.3 cm.
*Length.*—0.8 cm to 1.0 cm.
*Color.*—RHS 149D (Yellow-Green).

Inflorescence:
*Blooming habit.*—Continuous.
*Lastingness of individual blooms on plant.*—Approximately 1 week.
*Fragrance.*—Absent.
*Inflorescence type.*—Raceme.
*Quantity of flowers and buds per flowering branch.*—10 to 12.

Flowers:
*Flower diameter* (*horizontal*).—2.1 cm.
*Flower height* (*vertical*).—0.5 cm to 0.6 cm.
*Mature flower.*—Upper lobe: Color, upper surface: Close to RHS 96B (Violet-Blue) with white margins. Length: 0.6 cm. Width: 0.4 cm. Shape: Spatulate. Apex: Mucronate. Margin: Entire. Texture (both upper and lower surfaces): Smooth. Lower lobe: Color, upper surface: Close to RHS 96B (Violet-Blue) with white margins. Color, lower surface: RHS 96D (Violet-Blue) with white margins. Length: 1.0 cm. Width: 0.9 cm. Shape: Orbicular. Apex: Mucronate. Margin: Entire.
*Corolla tube: Color inside: RHS N*155D (White) with RHS 96B (Violet-Blue) pattern of lines and dots. Color outside: RHS N155D (White) with RHS 96D (Violet-Blue) dots. Tube length: 0.7 cm. Diameter: 0.5 cm.
*Calyx.*—Length: 1.1 cm (can include an additional 0.3 cm for the fused part). Diameter: 0.2 cm (measured at the fusion point). Shape: Composed of 5 narrowly triangular single leaflets forming a star shaped calyx fused in the lower quarter. Apex: Narrowly acute. Texture: Smooth. Color: RHS 137A (Green).

Reproductive organs:
*Stamens.*—Quantity per flower: 5. Filament length: 0.7 cm. Filament color: RHS 97B (Violet-Blue). Anther length: 0.8 cm. Anther width: 0.1 cm. Anther color: RHS 94A (Violet-Blue). Pollen color: RHS 3D (Yellow). Pollen amount: Sparse.
*Pistils.*—Stigma shape: Discoid, in two parts. Stigma color: Immature: RHS not visible, appears in mature stage. Mature: RHS N79A (Purple). Style length: 0.8 cm. Style color: RHS 145D (Yellow-Green). Ovary color: RHS 145D (Yellow-Green). Ovary shape: Ovate.

Fruit and seed set: Fruit and seed set not observed.

Disease and pest/insect resistance: No disease and pest/insect resistance observed.

COMPARISON WITH PARENTAL LINES AND KNOWN VARIETY

'KLELE20103' can be distinguished from its parents as described in Table 1.

TABLE 1

Comparison with Parental Lines

| Characteristic | 'KLELE20103' | Female Parent 'LE-2015-5129' | Male Parent 'LE-2015-5135' |
|---|---|---|---|
| Petal color | Blue and white bicolor | White | |
| Stem strength | Medium | | Weak |

'KLELE20103' is most similar to the commercial *Lobelia* variety 'KLELE20100' (U.S. Plant patent application Ser. No. 17/373,323). Differences between the varieties are described in Table 2.

TABLE 2

Comparison with Similar Variety

| Characteristic | 'KLELE20103' | 'KLELE20100' |
|---|---|---|
| Petal color | Blue and white bicolor | Violet-blue with white centers |
| Habit | Upright | Semi-upright |

I claim:

1. A new and distinct variety of *Lobelia* plant designated 'KLELE20103' as illustrated and described herein.

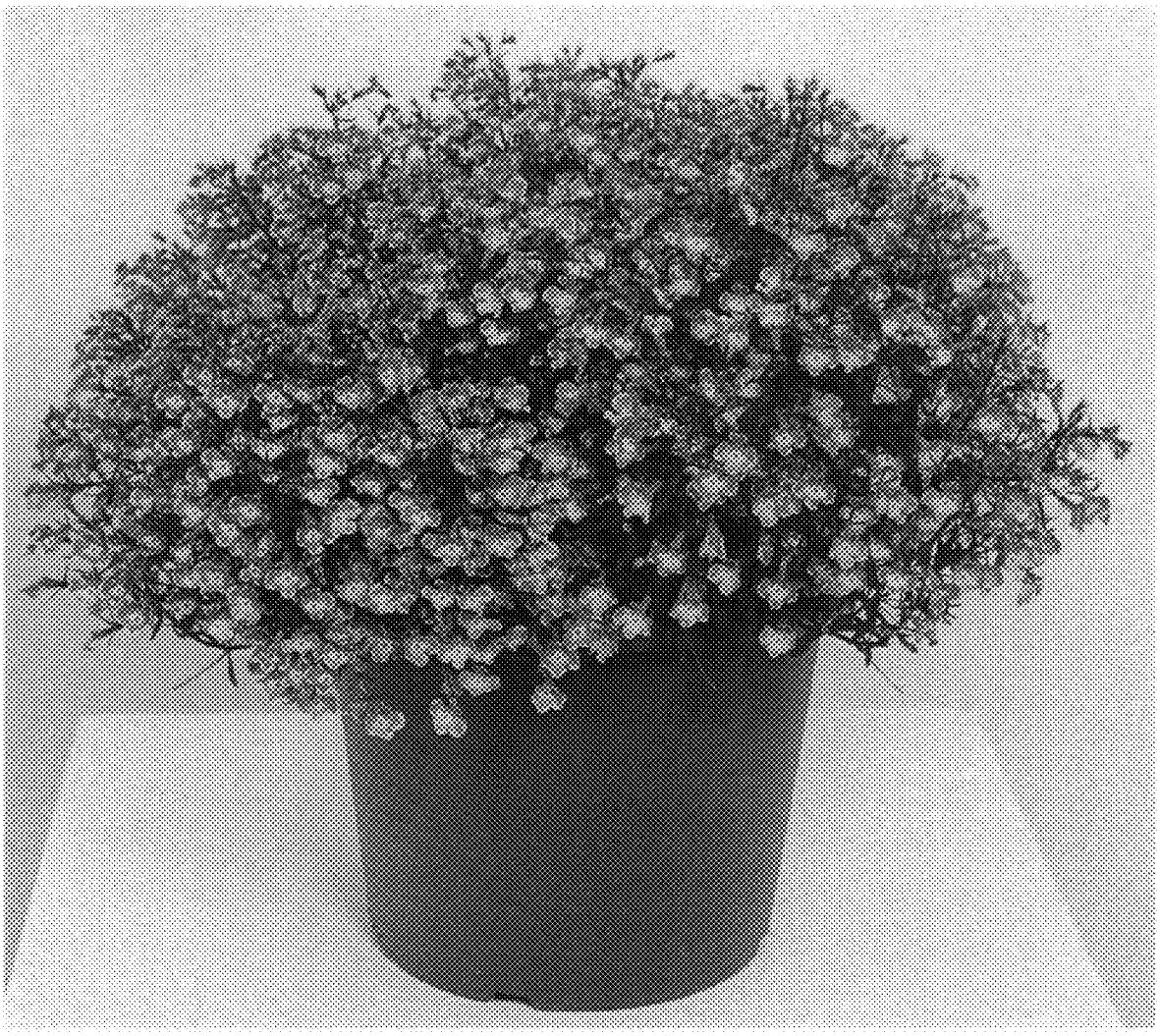

* * * * *